US00PP31070P2

(12) United States Plant Patent
Olesen

(10) Patent No.: US PP31,070 P2
(45) Date of Patent: Nov. 19, 2019

(54) ***ROSA* HYBRID NAMED 'POULPAR107'**

(50) Latin Name: ***Rosa* hybrid**
Varietal Denomination: Poulpar107

(71) Applicant: Mogens Nyegaard Olesen, Fredensborg (DK)

(72) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 15/999,580

(22) Filed: Sep. 4, 2018

(51) Int. Cl.
*A01H 5/02* (2018.01)
*A01H 6/74* (2018.01)

(52) U.S. Cl.
USPC ..... Plt./118

(58) Field of Classification Search
USPC ..... Plt./118
CPC ..... A01H 5/02; A01H 6/74
See application file for complete search history.

(56) References Cited

PUBLICATIONS

PLUTO Plant Variety Database Mar. 29, 2019.*
http://www.helpmefind.com/gardening/l.php?l=2.81745 Apr. 1, 2019.*

* cited by examiner

*Primary Examiner* — Annette H Para

(57) ABSTRACT

A new garden rose plant of the miniature class which has abundant, yellow flowers and attractive foliage. This new and distinct variety has shown to be uniform and stable in the resulting generations from asexual propagation.

1 Drawing Sheet

Botanical designation: *Rosa* hybrid.
Variety denomination: 'Poulpar107'.

SUMMARY OF THE INVENTION

The present invention constitutes a new and distinct variety of rose plant which originated from a controlled crossing between the female seed parent, an unnamed seedling referenced by the breeder as 06/0781-03, and the male pollen parent, also an unnamed seedling referenced by the breeder as 05/1100-06. Both of the parent varieties are non-patented.

The two parents were crossed during the summer of 2007 and the resulting seeds were planted in a controlled environment in Fredensborg, Denmark. The new variety, named 'Poulpar107', originated as a single seedling from the stated cross.

The new variety may be distinguished from its male pollen parent and female seed parent primarily by the following characteristics. The male pollen parent plant has a growth height of 50-60 cm while the new variety has a growth height of about 30 cm. The female seed parent plant has orange flowers while the new variety has yellow flowers.

The objective of the hybridization of this rose variety was to create a new and distinct variety with unique qualities, such as:

1. Uniform and abundant yellow flowers;
2. Vigorous, but compact growth when propagated on its own roots;
3. Exceptional disease resistance.

This combination of qualities is not present in previously available commercial cultivars of this type, known to the inventor, and distinguish 'Poulpar107' from all other varieties of which we are aware.

As part of the rose development program, Mogens N. Olesen germinated the seeds from the aforementioned hybridization during winter of 2007 and conducted evaluations on the resulting seedlings in a controlled environment in Fredensborg, Denmark. 'Poulpar107' was selected in the spring of 2008 by the inventor as a single plant from the progeny of the aforementioned hybridization.

Asexual reproduction of 'Poulpar107' by rooted cuttings was first done by Mogens N. Olesen in the nursery in Fredensborg, Denmark in July, 2008. This initial and other subsequent asexual propagations conducted in controlled environments have demonstrated that the characteristics of 'Poulpar107' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poulpar107'. Specifically illustrated in the drawing are a flowering branch showing flowers upon opening, an open flower viewed from above, flower petals detached, sepals detached showing reproductive flower parts, a bare stem, and mature leaf. Plants shown are 2 years of age.

DETAILED DESCRIPTION OF THE VARIETY

The following is a description of 'Poulpar107', as observed in its growth in a field nursery in Marion County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulpar090', U.S. Plant Pat. No. 28,044 are compared to 'Poulpar107' in Chart 1.

CHART 1

| | 'Poulpar107' | 'Poulpar090' |
|---|---|---|
| Petal Count | 85 to 90 | 80 |
| Flower Diameter | 65 mm | 70 mm |
| General Tonality of Flower Color | Yellow Orange Group 20B | Yellow-Orange Group 20D |

FLOWER AND FLOWER BUD

Blooming habit: Continuous.

Flower bud:

*Size.*—Upon opening, 25 mm in length from base of receptacle to end of bud. Bud diameter is 12 mm.

*Bud form.*—Ovoid.

*Bud color.*—As sepals divide petals are Yellow-Orange Group 14D with other intonations of Green Yellow Group 1D.

*Sepal inner surface.*—Color: Yellow-Green Group 146D. Surface: Lightly pubescent.

*Sepal outer surface.*—Color: Yellow-Green Group 144A. Texture: Smooth.

*Sepal shape.*—Apex: Cirrhose. Base: Flat at union with receptacle.

*Sepal margin.*—Margins have weak foliaceous appendages on three of the five sepals.

*Sepal size.*—About 20 mm long, 6 mm wide.

*Receptacle.*—Texture: Smooth. Size: 5 mm in height, 7 mm wide. Color: Yellow-Green Group 144A. Shape: Funnel.

*Pedicel.*—Surface: Smooth. Length: About 25 mm. Diameter: 2.5 mm on average. Color: Yellow-Green Group 144A. Strength: Strong.

*Peduncle.*—Length: 5 to 10 cm. Diameter: About 3 mm. Color: Yellow-Green Group 145A. Texture: Smooth.

Flower bud development: Flower buds are borne singly or in clusters of 3 to 5 flower buds per stem.

Flower bloom:

*Fragrance.*—None.

*Duration.*—The blooms have a duration on the plant of approximately 21 days. Petals fall cleanly away from plant after flowers have fully matured.

*Size.*—Flower diameter is about 65 mm when open. Flower depth is 20 mm.

*Flower shape.*—High centered double, with a high pointed center which is tightly closed.

*Shape of flower, side view.*—The upper portion is flat. The lower portion is flat.

Petalage: Under normal conditions, flowers have about 85 to 90 petals.

General tonality of flower: Open flowers are Yellow Orange Group 20B.

Petal color:

*Upon opening, outer petals.*—Upper surface: Yellow Group 6D and Yellow Group 12B. Lower surface: Yellow-Orange Group 16C and Yellow Group 6D. Light intonations of Green Yellow Group 1D also observed.

*Upon opening, inner petals.*—Upper surface: Yellow-Orange Group 21B splashed with Yellow-Orange Group 16C at the basal zone. Lower surface: Yellow-Orange Group 21D.

*Basal petal spots, upon opening.*—No distinctive coloration.

*After opening, outer petals.*—Upper surface: Yellow Group 6D and Yellow Group 12C. Lower surface: Yellow-Orange Group 16D and Yellow Group 4D.

*After opening, inner petals.*—Upper surface: Yellow-Orange Group 21C splashed with Yellow-Orange Group 16C Lower surface: Yellow-Orange Group 21D.

*Basal petal spots, after opening.*—No distinctive coloration.

Petals:

*Petal reflex.*—Somewhat reflexed.

*Margin.*—Entire with undulations.

*Shape.*—Broad and elliptic. Apex shape: Rounded with a point at the apex. Base shape: Acute.

*Size.*—About 30 mm (l)×25 to 30 mm (w).

*Texture.*—Smooth.

*Thickness.*—Average.

Petaloids:

*Size.*—12 mm (l) by 6 mm (w).

*Quantity.*—10 to 15.

*Shape.*—Elliptical with an acute base and rounded apices.

*Color.*—Yellow-Orange Group 21B on the upper surface, and Yellow-Orange Group 16C on the undersurface. Shades of Yellow Group 12C toward the petaloid base.

Reproductive flower parts:

*Pollen.*—None observed.

*Anthers.*—Size: 1.5 mm in length. Color: Greyed-Yellow Group 160C. Quantity: 35 to 40.

*Filaments.*—Color: Orange-Red Group 34C. Length: 6 mm.

*Pistils.*—Length: 5 mm. Quantity: 20 on average.

*Stigmas.*—Color: Green-White Group 157A.

*Styles.*—Color: Green-White Group 157A.

*Location of stigmas.*—Inferior in location relative to the length of the filaments and the height of the anthers.

*Hips.*—None Observed.

PLANT

Plant growth: Upright. Plants are about 35 cm in height, and 30 cm wide.

Stems:

*Color of juvenile growth.*—Yellow-Green Group 144B.

*Color of mature growth.*—Yellow-Green Group 144A.

*Length.*—Canes are about 15 cm from the base of the plant to the flowering portion.

*Diameter.*—About 5 mm.

*Internodes.*—On mature canes about 23 mm between nodes.

*Surface texture.*—Young wood: Smooth. Older wood: Partially rough with small prickles.

Long prickles:

*Incidence.*—5 prickles per 10 cm of stem.

*Size.*—Average length of prickles on mature stems is 5 mm.

*Shape*.—Upper portion is linear. Lower portion is concave.

*Color*.—Juvenile prickles: Greyed-Red Group 181A. Mature prickles: Greyed-Red Group 181A.

Plant foliage:

*Compound leaf*.—75 mm (l)×50 (w).

*Quantity*.—3 or 4 leaves per 10 cm of stem on average.

*Leaf bearing angle to the stem*.—45 degrees.

*Color of juvenile foliage*.—Upper side: Yellow-Green Group 144A. Lower side: Yellow-Green Group 144B.

*Color of mature foliage*.—Upper side: Yellow-Green Group 147A. Lower side: Yellow-Green Group 146C.

Plant leaves and leaflets:

*Stipules*.—Size: 13 mm long, 3 mm wide. Quantity: 2 per compound leaf. Shape: Linear, slightly broad based with outward extending apices. Margins: Finely serrated. Color: Yellow-Green Group 144A.

*Petiole*.—Length: 13 mm. Diameter: 2 mm. Upper surface color: Yellow-Green Group 144A. Lower surface color: Yellow-Green Group 144A.

*Rachis*.—Length: 20 mm. Upper surface color: Yellow-Green Group 144A. Lower surface color: Yellow-Green Group 144A.

*Leaflet*.—Quantity: Normally 5 leaflets. Margins: Serrated. Size: Terminal leaflets are about 42 mm long, 22 mm wide. Shape: Generally elliptical. Base: Rounded. Apex: Acute. Texture: Smooth. Thickness: Average. Arrangement: Odd pinnate. Venation: Reticulate. Glossiness: Not glossy.

Disease resistance: Above average resistance to powdery mildew *Sphaerotheca pannosa*, downy mildew *Peronospora sparsa*, rust *Phragmidium* sps., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the miniature rose class named 'Poulpar107', substantially as illustrated and described herein, due to its abundant yellow flowers, disease resistance, and extended period of bloom.

* * * * *

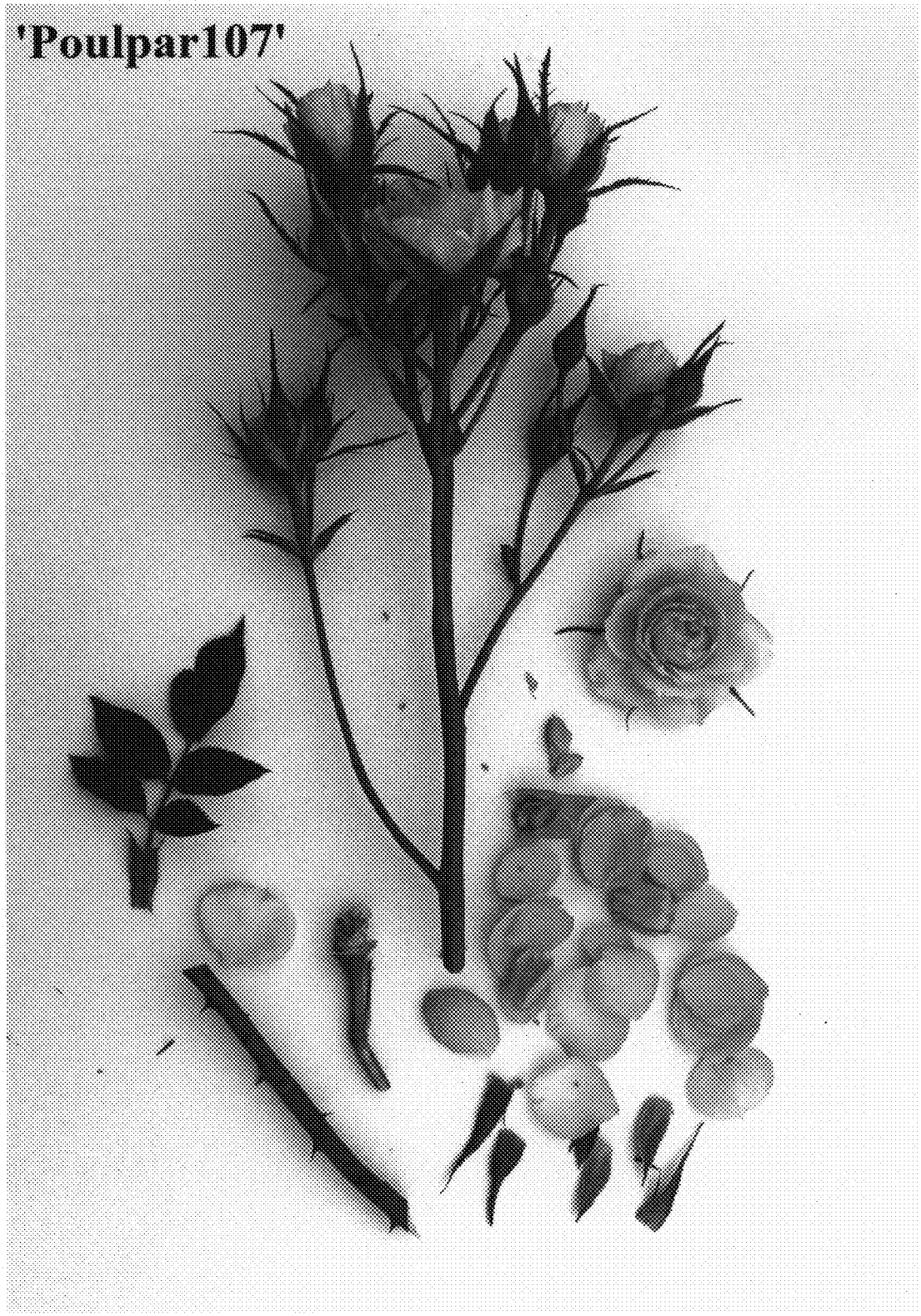
'Poulpar107'